United States Patent
May et al.

(10) Patent No.: US 9,050,143 B2
(45) Date of Patent: Jun. 9, 2015

(54) SPINAL CORRECTION SYSTEM

(71) Applicant: Warsaw Orthopedic, Inc., Warsaw, IN (US)

(72) Inventors: Jason M. May, Cordova, TN (US); Molly K Rice, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/915,259

(22) Filed: Jun. 11, 2013

(65) Prior Publication Data

US 2014/0364912 A1    Dec. 11, 2014

(51) Int. Cl.
*A61B 17/70*    (2006.01)

(52) U.S. Cl.
CPC ......... *A61B 17/7043* (2013.01); *A61B 17/7002* (2013.01)

(58) Field of Classification Search
CPC .................. A61B 17/7043; A61B 17/7002
USPC ................ 606/246, 86 A, 86 R, 99, 104, 279
See application file for complete search history.

(56) References Cited

U.S. PATENT DOCUMENTS

| | | | | |
|---|---|---|---|---|
| 5,720,751 A * | 2/1998 | Jackson | ...................... | 606/86 R |
| 5,951,564 A * | 9/1999 | Schroder et al. | ............... | 606/100 |
| 6,183,472 B1 * | 2/2001 | Lutz | ............................ | 606/86 A |
| 7,621,918 B2 * | 11/2009 | Jackson | ...................... | 606/86 A |
| 7,824,411 B2 * | 11/2010 | Varieur et al. | ............... | 606/86 A |
| 2009/0018593 A1 * | 1/2009 | Barrus et al. | ................. | 606/86 A |

* cited by examiner

*Primary Examiner* — Pedro Philogene
*Assistant Examiner* — David Comstock (57) ABSTRACT

An implant support comprises a first member including a first portion and a second portion configured to engage a bone fastener. The second portion extends in a transverse orientation from the first portion. The members define a longitudinal axis. The second member includes a first portion and a second portion configured to engage the bone fastener. The second portion of the second member extends in a transverse orientation from the first portion. At least one of the members is movable relative to the longitudinal axis between a first configuration and a second configuration such that the longitudinal axis is offset relative to an axis of the bone fastener. Systems and methods are disclosed.

20 Claims, 8 Drawing Sheets

FIG. 13

SPINAL CORRECTION SYSTEM

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments may employ surgical instruments engageable with implants that are manipulated for connection with vertebrae to position and align one or more vertebrae. This disclosure describes an improvement over these prior art technologies.

SUMMARY

In one embodiment, an implant support is provided. The implant support comprises a first member including a first portion and a second portion configured to engage a bone fastener. The second portion extends in a transverse orientation from the first portion. A second member is connected to the first member such that the members define a longitudinal axis. The second member includes a first portion and a second portion configured to engage the bone fastener. The second portion of the second member extends in a transverse orientation from the first portion of the second member. At least one of the members is movable relative to the longitudinal axis between a first configuration and a second configuration such that the members are connected to the bone fastener and the longitudinal axis is offset relative to an axis of the bone fastener. In some embodiments, systems and methods are provided.

BRIEF DESCRIPTION OF THE DRAWINGS

The present disclosure will become more readily apparent from the specific description accompanied by the following drawings, in which.

DETAILED DESCRIPTION

The exemplary embodiments of the spinal correction system and related methods of use disclosed are discussed in terms of medical devices for the treatment of musculoskeletal disorders and more particularly, in terms of a spinal correction system and method that facilitates connection of at least one implant with vertebrae to position and align one or more vertebrae for treatment of a spine. In some embodiments, the spinal correction system can include instruments such as extenders, reducers and translators, which can be used to introduce a vertebral construct such as a rod to a bone fastener, such as a bone anchor or bone screw. For example, an instrument can include an extender having bone anchor attachment features on one or both sides of the instrument. In some embodiments, the extender may be used with or include a reducer assembly to introduce a spinal rod into a bone fastener.

In one embodiment, the system is employed with a method for deformity correction, such as, for example, those techniques that require a plurality of rod reducers for correction. For example, correction of a right thoracic adolescent idiopathic scoliosis (AIS) curve can employ several rod reducers that are connected to bone screws attached with a concavity of vertebrae. In one embodiment, the system includes a rod reducer having a low profile configuration in a sagittal plane of vertebrae. This configuration allows for movement of the rod reducer in the sagittal plane to accommodate anatomy and various bone screw types. In one embodiment, the rod reducer includes a clamping mechanism that attaches to a bone screw head. The clamping mechanism resists and/or prevents disengagement of the rod reducer from the bone screw during deformity correction maneuvers such as rod rotation and direct vertebral derotation.

In one embodiment, the system includes a low profile spinal rod reducer that allows for clamping onto a bone screw. In one embodiment, the rod reducer is offset from a center axis of a bone screw such that a set screw is directly introduced into the bone screw without going through the rod reducer. In one embodiment, the engagement of the rod reducer with the bone screw allows the rod reducer to move, rock and/or sway in a sagittal plane of vertebrae to accommodate anatomy and bone screw types, such as, for example, multi-axial screws (MAS), sagittal adjusting screws (SAS) and fixed axial screws (FAS). In one embodiment, the system is employed with a method for deformity correction, such as, for example, correction of a lumbar scoliosis. In some embodiments, the system is employed with a method and sequence to efficiently correct various deformity pathologies in sagittal, coronal and axial planes of vertebrae while minimizing stress on bone/screw interfaces by using bone screws and reduction instruments.

In some embodiments, the system is employed for axial derotation of vertebral bodies to improve chest wall volume and pulmonary function. In one embodiment, the system includes pedicle screws placed in the vertebral bodies that provide anchors for spinal manipulation. In one embodiment, the system includes implant supports, such as, for example, reduction instruments attached to the pedicle screws that are configured as derotation levers. In one embodiment, the system includes implant supports, such as, for example, reduction instruments that are linked together. In one embodiment, the system includes a tightening/derotation handle.

In some embodiments, the spinal correction system may include instruments that are connected or attached to an instrument(s) such as, for example, a lateral translation handle or derotation instruments. In one embodiment, one or all of the components of the surgical system are disposable, peel-pack, pre-packed sterile devices used with a spinal correction system. One or all of the components of the spinal correction system may be reusable. The spinal correction system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a spinal correction system and related methods of employing the system in accordance with the principles of the present disclosure. Alternate embodiments are also disclosed. Reference will now be made in detail to the exemplary embodiments of the present disclosure, which are illustrated in the accompanying figures. Turning to FIGS. 1-7, there are illustrated components of a surgical system, such as, for example, a spinal correction system 10 in accordance with the principles of the present disclosure.

The components of spinal correction system 10 can be fabricated from biologically acceptable materials suitable for medical applications, including metals, synthetic polymers, ceramics and bone material and/or their composites, depending on the particular application and/or preference of a medical practitioner. For example, the components of spinal correction system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKEL-ITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglyclolide, polytyrosine carbonate, polycaroplaetohe and their combinations. Various components of spinal correction system 10 may have material composites, including the above materials, to achieve various desired characteristics such as strength, rigidity, elasticity, compliance, biomechanical performance, durability and radiolucency or imaging preference. The components of spinal correction system 10, individually or collectively, may also be fabricated from a heterogeneous material such as a combination of two or more of the above-described materials. The components of spinal correction system 10 may be monolithically formed, integrally connected or include fastening elements and/or instruments, as described herein.

Spinal correction system 10 is employed, for example, with an open or mini-open, minimal access and/or minimally invasive including percutaneous surgical technique for engagement with an implant, such as, for example, a bone fastener for a correction treatment at a surgical site within a body of a patient, for example, a section of a spine to treat various spine pathologies, such as, for example, AIS and Scheuermann's kyphosis. In one embodiment, the components of spinal correction system 10 are configured to deliver and introduce an implant, such as, for example, a vertebral construct such as a rod to a bone fastener.

Spinal correction system 10 includes an implant support 11 having a first member, such as, for example, an arm 12. Arm 12 includes a first portion, such as, for example, an extension 14 that defines an axis a. Extension 14 has a cylindrical cross section configuration. In some embodiments, all or only a portion of extension 14 may have alternate cross section configurations, such as, for example, oval, oblong, triangular, square, polygonal, irregular, uniform, non-uniform, offset, staggered, undulating, arcuate, variable and/or tapered. In some embodiments, all or only a portion of extension 14 may be alternately axially configured, such as, for example, uniform, non-uniform, offset, staggered, undulating, arcuate, variable and/or tapered.

Arm 12 includes a second portion, such as, for example, a leg 16 extending transversely from extension 14. Leg 16 defines an axis b that extends transversely from axis a. In some embodiments, leg 16 may extend from extension 14 at alternate orientations such that axis b is disposed relative to axis a, such as, for example, perpendicular and/or other angular orientations such as acute or obtuse, co-axial and/or may be offset or staggered.

Figure 1:
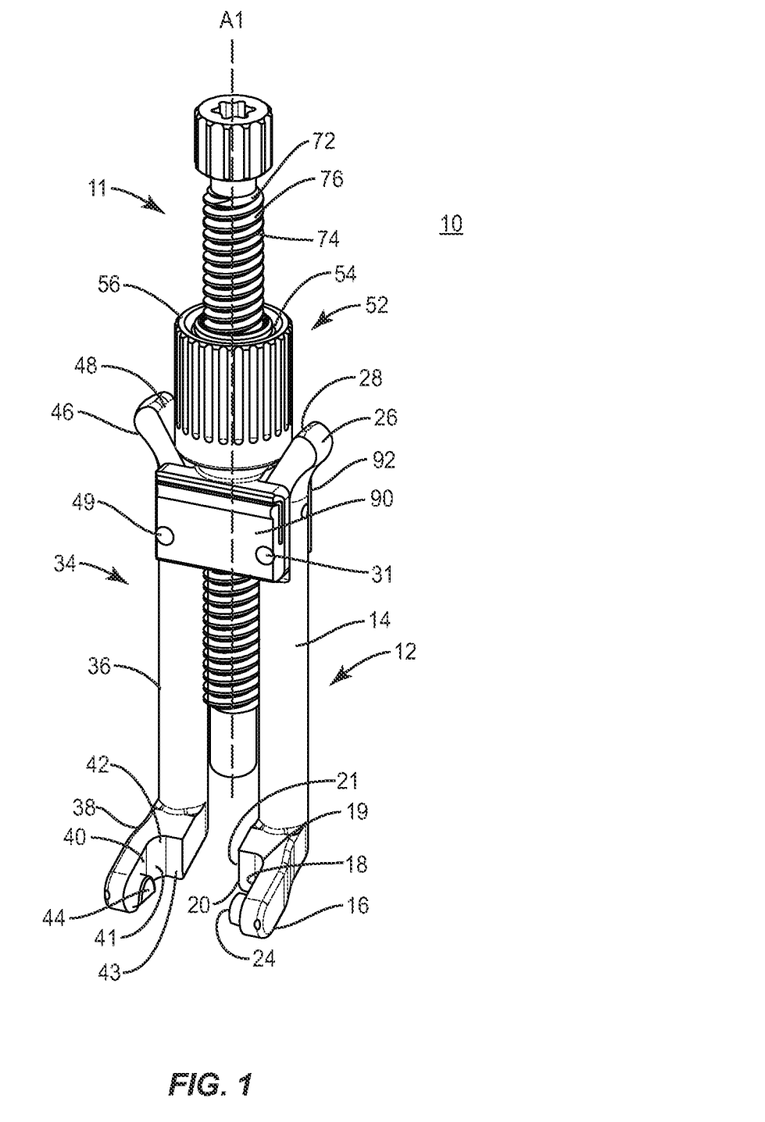
FIG. 1 is a perspective view of components of one embodiment of a system in accordance with the principles of the present disclosure.
Figure 2:
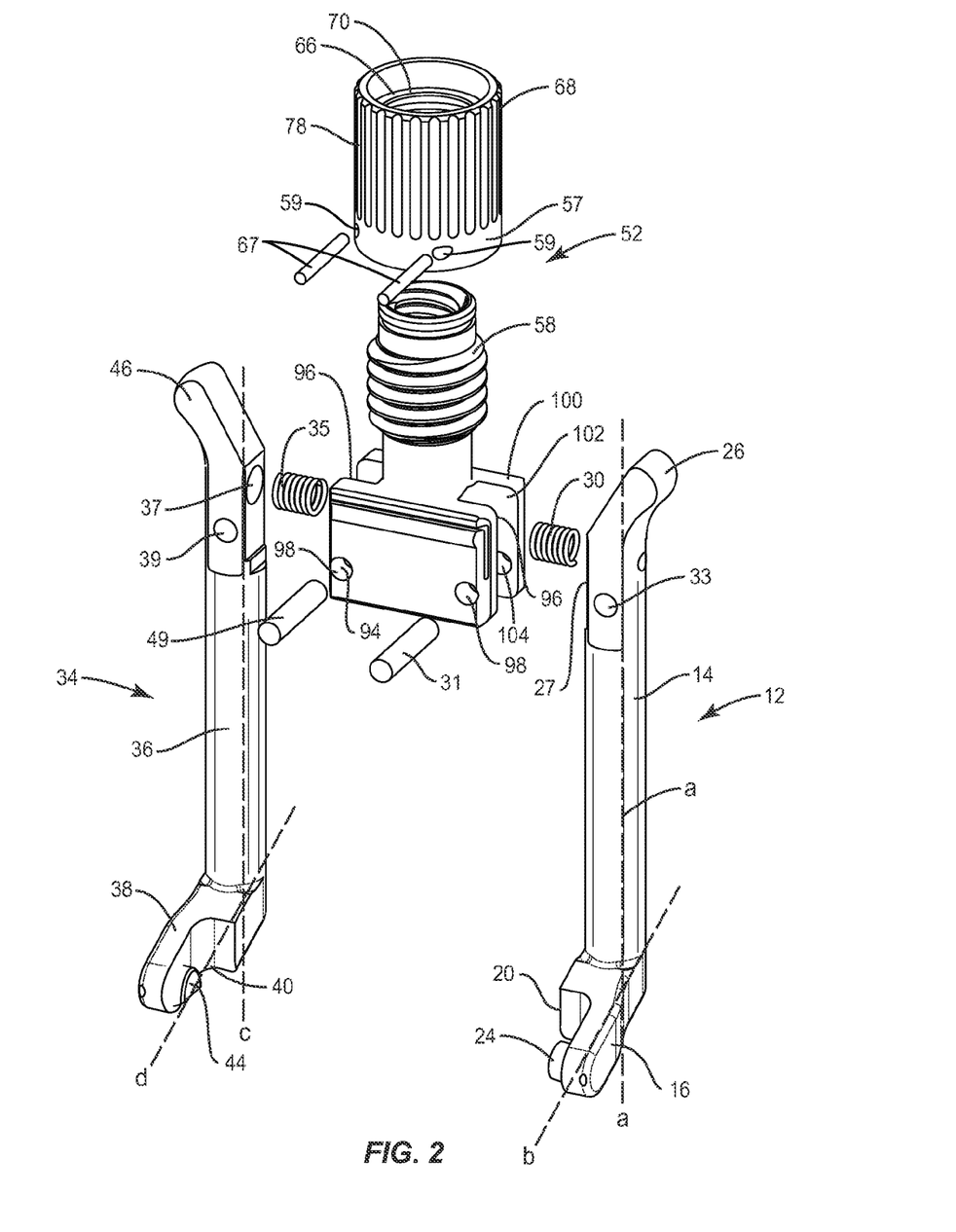
FIG. 2 is a perspective view of the components shown in FIG. 1 with parts separated.
Figure 3:
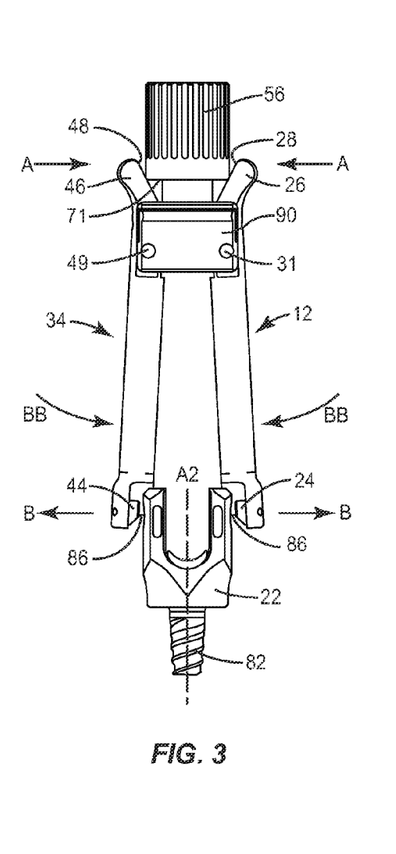
FIG. 3 is a plan view of components of one embodiment of a system in accordance with the principles of the present disclosure.

Leg 16 includes a surface 18 that defines a support cavity 20. Cavity 20 is configured for disposal of at least a portion of a fastener, such as, for example, a bone fastener 22, as shown in FIG. 3. Surface 18 includes a planar portion 19 and an angled portion 21. Portion 19 is configured to surround and/or engage a portion of a receiver of bone fastener 22. Portion 21 is configured to define a gap 32, discussed herein, between portion 21 and an outer surface of the receiver of bone fastener 22. Surface 18 defines a cylindrical tab 24 projecting into cavity 20 and configured for releasably capturing bone fastener 22. In some embodiments, all or only a portion of surface 18 may have alternate surface configurations to enhance fixation with bone fastener 22, such as, for example, rough, arcuate, undulating, mesh, porous, semi-porous, dimpled and/or textured.

Figure 4:
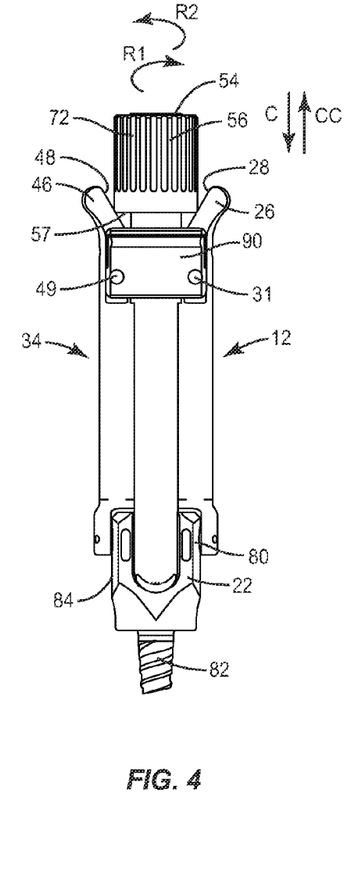
FIG. 4 is a plan view of the components shown in FIG. 3.
Figure 6:
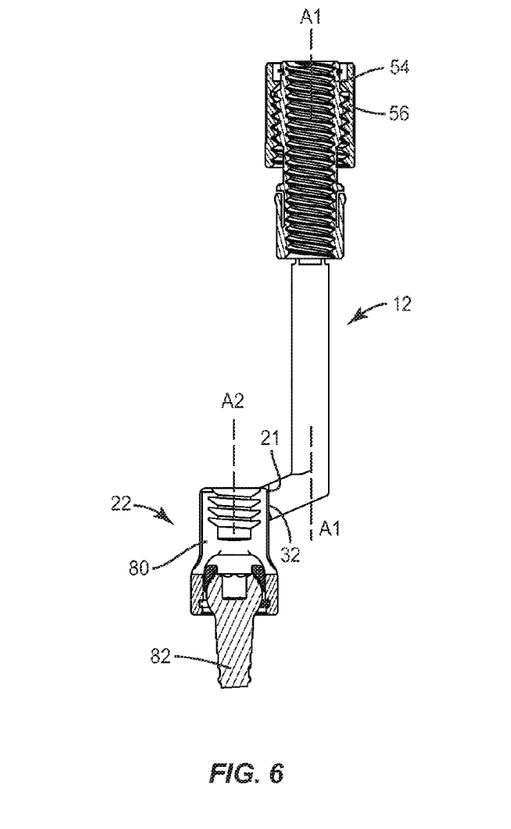
FIG. 6 is a side cross section view of the components shown in FIG. 4.
Figure 7:
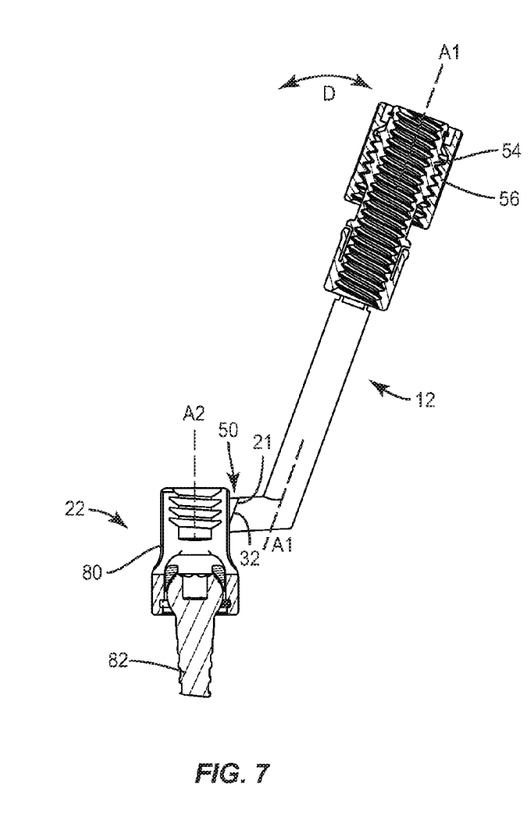
FIG. 7 is a side cross section view of the components shown in FIG. 4.

In one embodiment, arm 12 is movable between a first, open configuration, as shown in FIG. 3, and a second, closed configuration, as shown in FIG. 4, such that tab 24 is removably fixed within a cavity of the outer surface of bone fastener 22 and bone fastener 22 is captured by arm 12 within cavity 20. In one embodiment, in the second configuration, gap 32 is disposed such that arm 12 is rotatable about bone fastener 22 within a plane of a body between a first orientation, as shown in FIG. 6, and a second orientation, as shown in FIG. 7, as discussed herein.

Arm 12 includes a transverse end 26 that is manipulable to rotate arm 12 for pivotal movement about a body, described herein, of implant support 11 between the first configuration and the second configuration. End 26 is configured for engagement with a locking part 56, discussed herein. End 26 includes an inner surface 28 configured for fixation with part 56 to lock arm 12 in the second configuration. In one embodiment, surface 28 is angled for slidable engagement with part 56 such that part 56 slides along surface 28 to rotate arm 12 about the body and for fixation with part 56 to lock arm 12 in the second configuration.

Implant support 11 includes a second member, such as, for example, an arm 34. Arm 34 is connected to arm 12 to define a longitudinal axis A1 of implant support 11. Arm 34 includes a first portion, such as, for example, an extension 36 that defines an axis c. Extension 36 has a cylindrical cross section configuration. In some embodiments, all or only a portion of extension 36 may have alternate cross section configurations, such as, for example, oval, oblong, triangular, square, polygonal, irregular, uniform, non-uniform, offset, staggered, undulating, arcuate, variable and/or tapered. In some embodiments, all or only a portion of extension 36 may be alternately axially configured, such as, for example, uniform, non-uniform, offset, staggered, undulating, arcuate, variable and/or tapered.

Arm 34 includes a second portion, such as, for example, a leg 38 extending transversely from extension 36. Leg 38 defines an axis d that extends transversely from axis c. In some embodiments, leg 38 may extend from extension 36 at alternate orientations such that axis c is disposed relative to axis d, such as, for example, perpendicular and/or other angular orientations such as acute or obtuse, co-axial and/or may be offset or staggered.

Leg 38 includes an inner surface 40 that defines a support cavity 42. Cavity 42 is configured for disposal of at least a portion of bone fastener 22. Surface 40 includes a planar portion 41 and an angled portion 43. Portion 41 is configured to surround and/or engage a portion of the outer surface of bone fastener 22. Portion 43 is configured to define a gap 50, discussed herein, between portion 43 and the outer surface of bone fastener 22. Surface 40 defines a cylindrical tab 44 projecting into cavity 42 and configured for releasably capturing bone fastener 22. In some embodiments, all or only a portion of surface 40 may have alternate surface configurations to enhance fixation with bone fastener 22, such as, for example, rough, arcuate, undulating, mesh, porous, semi-porous, dimpled and/or textured.

In one embodiment, arm 34 is movable between a first, open configuration, as shown in FIG. 3, and a second, closed configuration, as shown in FIG. 4, such that tab 44 is removably fixed within a cavity of the receiver of bone fastener 22 and bone fastener 22 is captured by arm 34 within cavity 42. In one embodiment, in the second configuration, gap 50 is disposed such that arm 34 is rotatable about bone fastener 22 within a plane of a body between a first orientation, as shown in FIG. 6, and a second orientation, as shown in FIG. 7, as discussed herein.

Arm 34 includes a transverse end 46 that is manipulable to rotate arm 34 for pivotal movement about a body, described herein, of implant support 11 between the first configuration and the second configuration. End 46 is configured for engagement with part 56, discussed herein. End 46 includes an inner surface 48 configured to engage part 56 to lock arm 34 in the second configuration. In one embodiment, surface 48 is angled for slidable engagement with part 56 such that part 56 slides along surface 48 to rotate arm 34 about the body and for fixation with part 56 to lock arm 34 in the second configuration.

Implant support 11 includes a body 52 configured to connect arm 12 and arm 34 such that arms 12, 34 define axis A1, as shown in FIGS. 6 and 7. Body 52 includes a plate 90 and a plate 92, which are attached to arms 12, 34 and facilitate pivotal movement of arms 12, 34 relative thereto. Plate 90 includes a surface 94 that defines cavities 98 configured to support pins 31, 49. Plate 92 includes a surface 100 that defines cavities 104 configured to support pins 31, 49.

Pin 31 extends through a cavity 33 of arm 12 to connect arm 12 with body 52. Pin 31 facilitates rotation of extension 14 relative to plates 90, 92 such that arm 12 is pivotable about pin 31 and the connection of arm 12 with body 52. Pin 49 extends through a cavity 39 of arm 34 to connect arm 34 with body 52. Pin 49 facilitates rotation of extension 36 relative to plates 90, 92 such that arm 34 is pivotable about pin 49 and the connection of arm 34 with body 52. Ends 26, 46 are manipulable to rotate arms 12, 34 for pivotal movement about pins 31, 49 between the first configuration and the second configuration, described herein.

In one embodiment, arms 12, 34 are manipulable to a first, open configuration, as shown in FIG. 3, and resiliently biased to a second, closed configuration, as shown in FIG. 4.

In one embodiment, surfaces 94, 100 define cavities 96 configured to support a biasing member, such as, for example, a spring 30 and/or a spring 35. End 26 defines a cavity 27 configured for disposal of spring 30. As arm 12 is rotated to the first configuration, the bias of spring 30 is overcome and spring 30 is compressed within cavity 27. Spring 30 is biased to expand within cavity 27. End 26 is releasable such that spring 30 expands to engage body 52. As such, extension 14 is biased to rotate relative to body 52 and arm 12 is biased to pivot about pin 31 to the second configuration.

End 46 defines a cavity 37 configured for disposal of spring 35. As arm 34 is rotated to the first configuration, the bias of spring 35 is overcome and spring 35 is compressed within cavity 37. Spring 35 is biased to expand within cavity 37. End 46 is releasable such that spring 35 expands to engage body 52. As such, extension 36 is biased to rotate relative to body 52 and arm 34 is biased to pivot about pin 49 to the second configuration.

In one embodiment, arms 12, 34 rotate and/or pivot relative to body 52 together. In one embodiment, arms 12, 34 rotate and/or pivot relative to body 52 separately. In some embodiments, the biasing member may have a semi-rigid, rigid or elastic configuration, and/or have elastic properties, such as the elastic properties corresponding to the material examples described above, such that the biasing member provides a selective amount of expansion, contraction, collapse and/or extension. In some embodiments, the biasing member may include a plurality of separately attachable or connectable portions or sections, such as bands or loops, or may be monolithically formed as a single continuous element. In one embodiment, the biasing member includes an axial element, such as, for example, a flexible shaft. In one embodiment, the biasing member has a solid disc or sphere shape. In one embodiment, the biasing member has a tubular wall. In some embodiments, the biasing member may include an elastomeric member, clip, leaf spring, gravity induced configuration, pneumatic configuration, hydraulic configuration and/or manual lever.

Body 52 includes a tubular part 54 connected with plates 90, 92. Part 54 has a cylindrical cross section configuration and includes an outer surface 58 having a thread form 60 configured for threaded engagement with part 56 and a non-threaded portion 63. Threads 60 engage part 56 to facilitate axial translation of part 56 relative to part 54 between a first, non-locking position and a second position to lock arms 12, 34 in a selected configuration, as described herein. Part 54 includes an inner surface 62 defining an internal thread form 64 configured to engage a reduction instrument, described herein, to facilitate axial translation of the reduction instrument relative to body 52 for reducing an implant with bone fastener 22.

Part 56 includes an inner surface 66 and an outer surface 68. Surface 66 defines a thread form 70 engageable with thread form 60 to facilitate axial translation of part 56 relative to part 54. Part 56 includes an end surface 57 that defines cavities 59. Pins 67 are disposed in cavities 59 and are slidably disposed with the pitch of threads 60 in a pin and groove configuration to connect part 56 with part 54. Pins 67 prevent part 56 from disengaging from part 54. Surface 68 is configured to engage surfaces 28, 48 for locking arms 12, 34 in a selected configuration. In some embodiments, part 56 may be retained with part 54 by various components. For example, part 56 includes a groove 106 and part 54 includes a groove 108. Grooves 106, 108 are configured for disposal of a snap ring 110, which is oriented to retain part 56 with part 54 in a snap fit configuration.

Figure 5:
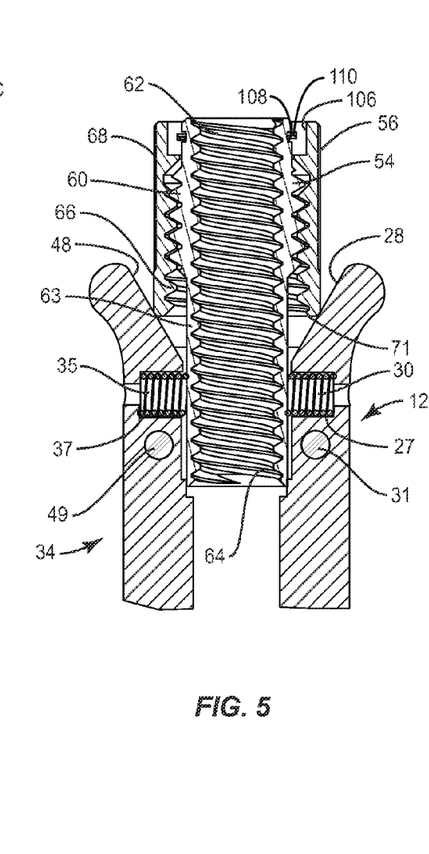
FIG. 5 is a break away cross section view of the components shown in FIG. 4.

In one embodiment, surface 68 includes a knurled gripping surface 78 to facilitate manipulation and/or rotation of part 56. In one embodiment, upon disposal of arms 12, 34 in a second, closed configuration, surface 78 is rotated in a clockwise direction to translate part 56 axially into engagement with arms 12, 34. Part 56 includes a corner surface 71 that frictionally engages surfaces 28, 48 to fix the surfaces and lock arms 12, 34 in the second configuration, as shown in FIG. 5.

Figure 13:
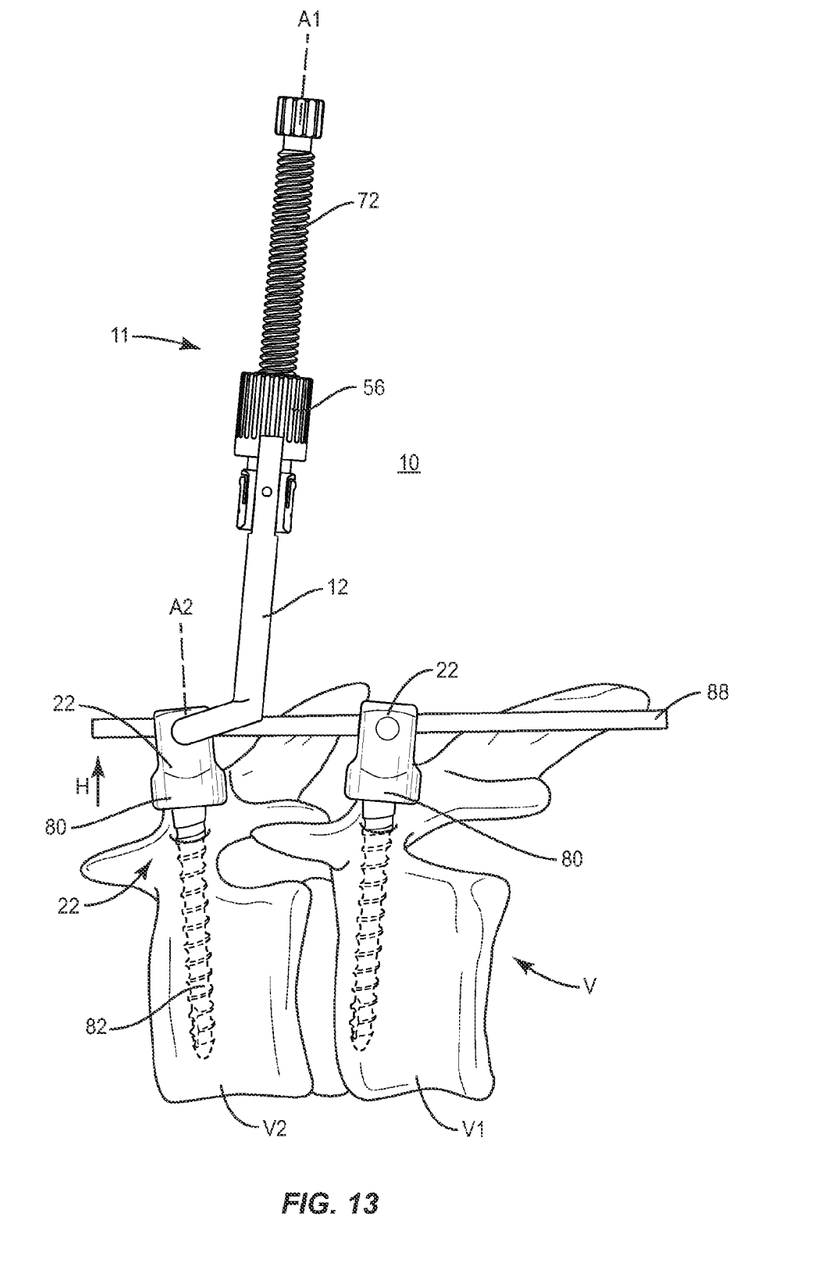
FIG. 13 is a side view of the components and vertebrae shown in FIG. 11.

In one embodiment, spinal correction system 10 includes bone fastener 22 for connecting a longitudinal element, such as, for example, a spinal rod 88, as shown in FIG. 13, to tissue, such as, for example, vertebrae and/or components of system 10, such as, for example, connectors, plates and other constructs, discussed herein. Bone fastener 22 defines a longitudinal axis A2, as shown in FIG. 6. Bone fastener 22 comprises a first portion, such as, for example, a receiver 80 and a second portion, such as, for example, an elongated shaft 82 configured for penetrating tissue.

Shaft 82 has a cylindrical cross section configuration and includes an outer surface having an external thread form. In some embodiments, the external thread form may include a single thread turn or a plurality of discrete threads. In some embodiments, other engaging structures may be located on shaft 82, such as, for example, a nail configuration, barbs, expanding elements, raised elements and/or spikes to facilitate engagement of shaft 82 with tissue, such as, for example, vertebrae.

In some embodiments, all or only a portion of shaft 82 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 82 may include one or a plurality of openings. In some embodiments, all or only a portion of the outer surface of shaft 82 may have alternate surface configurations to enhance fixation with tissue such as, for example, rough, arcuate, undulating, mesh, porous, semi-porous, dimpled and/or textured. In some embodiments, all or only a portion of shaft 82 may be disposed at alternate orientations, relative to axis A2, such as, for example, transverse, perpendicular and/or other angular orientations such as acute or obtuse, co-axial and/or may be offset or staggered. In some embodiments, all or only a portion of shaft 82 may be cannulated.

Receiver 80 includes a pair of spaced apart arms having an inner surface that defines a U-shaped passageway. The passageway is configured for disposal of an implant, such as, for example, spinal rod 88. In some embodiments, all or only a portion of the passageway may have alternate cross section configurations, such as, for example, oval, oblong, triangular, square, polygonal, irregular, uniform, non-uniform, offset, staggered, and/or tapered. In some embodiments, the arms of receiver 80 may be disposed at alternate orientations, relative to axis A2, such as, for example, transverse, perpendicular and/or other angular orientations such as acute or obtuse, co-axial and/or may be offset or staggered.

Receiver 80 includes an outer surface 84 defining cavities 86 configured for disposal of tabs 24, 44. Arms 12, 34 are movable between a first, open configuration, as shown in FIG. 3, and a second, closed configuration, as shown in FIG. 4, such that tabs 24, 44 are removably fixed within cavities 86 and bone fastener 22 is releasably captured by arms 12, 34 within cavities 20, 42. Implant support 11 captures bone fastener 22 such that implant support 11 includes a low profile configuration that allows for clamping onto bone fastener 22 such that axis A1 is offset from axis A2 in the second configuration. This offset configuration facilitates introduction of a set screw (not shown) along a trajectory and directly into bone fastener 22 without passing through implant support 11. In one embodiment, in the second configuration, axis A1 is offset and disposed in a substantially parallel orientation relative to axis A2. In one embodiment, in the second configuration, axis A1 is offset and disposed in a substantially transverse orientation relative to axis A2. In some embodiments, in the second configuration, axis A1 may be offset and disposed at alternate orientations, relative to axis A2, such as, for example, those alternatives described herein. In one embodiment, implant support 11 prevents disengagement from bone fastener 22 during deformity correction maneuvers such as rod rotation and direct vertebral derotation.

In one embodiment, spinal correction system 10 can include one or a plurality of bone fasteners such as those described herein and/or fixation elements, which may be engaged with tissue in various orientations, such as, for example, series, parallel, offset, staggered and/or alternate vertebral levels. In some embodiments, the bone fasteners and/or fixation elements may include one or a plurality of multi-axial screws, sagittal angulation screws, pedicle screws, mono-axial screws, uni-planar screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts. In some embodiments, spinal correction system 10 may comprise various instruments, such as, for example, inserters, extenders, reducers, spreaders, distractors, blades, retractors, clamps, forceps, elevators and drills, which may be alternately sized and dimensioned, and arranged as a kit.

In one embodiment, in operation, implant support 11 is manipulable to a first, open configuration, as shown in FIG. 3, and releasable and resiliently biased to a second, closed configuration, as shown in FIG. 4. From a closed configuration, as shown for example in FIG. 1, a manipulative force or pressure is applied to ends 26, 46, in the direction shown by arrows A in FIG. 3. Arms 12, 34 rotate outwardly to the first configuration, in the direction shown by arrows B. The bias of springs 30, 35 is overcome and springs 30, 35 are compressed, as described herein. In this configuration, arms 12, 34 are spaced apart to facilitate capture of receiver 80 of bone fastener 22. Ends 26, 46 are released and springs 30, 35 expand to engage body 52. Extensions 14, 36 are biased to rotate, in the direction shown by arrows BB, relative to body 52 and arms 12, 34 are biased to pivot to the second configuration. Tabs 24, 44 are removably fixed within cavities 86 and bone fastener 22 is releasably captured by arms 12, 34 within cavities 20, 42.

Surface 78 is rotated clockwise, in the direction shown by arrow R1 in FIG. 4, to translate part 56 axially, in the direction shown by arrow C, into engagement with arms 12, 34. Surface 71 frictionally engages surfaces 28, 48 to fix the surfaces and lock arms 12, 34 in the second configuration, as shown in FIG. 5.

In the second configuration, implant support 11 captures bone fastener 22 such that axis A1 is offset and disposed in a substantially parallel orientation relative to axis A2, as shown in FIG. 6 and described herein. Arms 12, 34 are rotatable about bone fastener 22 within a plane of a body, such as, for example, a sagittal plane between a first orientation such that axis A1 is offset and disposed in a substantially parallel orientation with axis A2 of bone fastener 22 and a second orientation such that axis A1 is offset and disposed in a substantially transverse orientation relative to axis A2 of bone fastener 22. Rotation of arms 12, 34, in the direction shown by arrows D in FIG. 7, relative to and about bone fastener 22 is facilitated by gaps 32, 50. Gaps 32, 50 allow movement and/or pivoting of arms 12, 34 such that implant support 11 is low profile and movable in the sagittal plane to accommodate patient anatomy, surgical instruments such as adjacent implant support(s), various bone fastener types and allow for a set screw (not shown) to be inserted into receiver 80 without interference from implant support 11 once spinal rod 88 is reduced, as discussed herein.

To disengage implant support 11 from bone fastener 22, surface 78 is rotated counter-clockwise, in the direction shown by arrow R2 in FIG. 4, to translate part 56 axially, in the direction shown by arrow CC, out of engagement with arms 12, 34. From the second, closed configuration, as shown in FIG. 4, a manipulative force or pressure is applied to ends 26, 46, in the direction shown by arrows A in FIG. 3. Arms 12, 34 rotate outwardly to the first configuration, in the direction shown by arrows B. The bias of springs 30, 35 is overcome and arms 12, 34 are spaced apart to facilitate release of bone fastener 22 from implant support 11.

Figure 8:
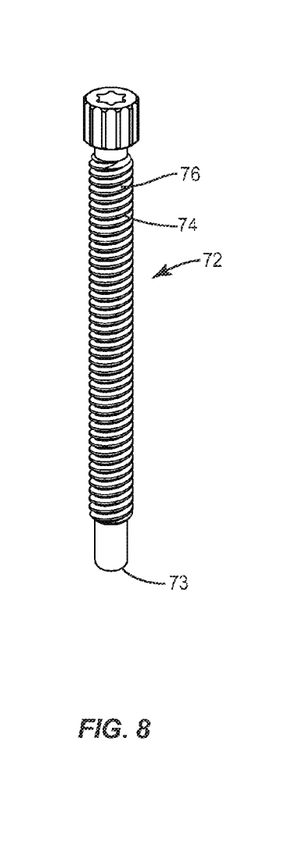
FIG. 8 is a perspective view of a component of one embodiment of a system in accordance with the principles of the present disclosure.
Figure 9:
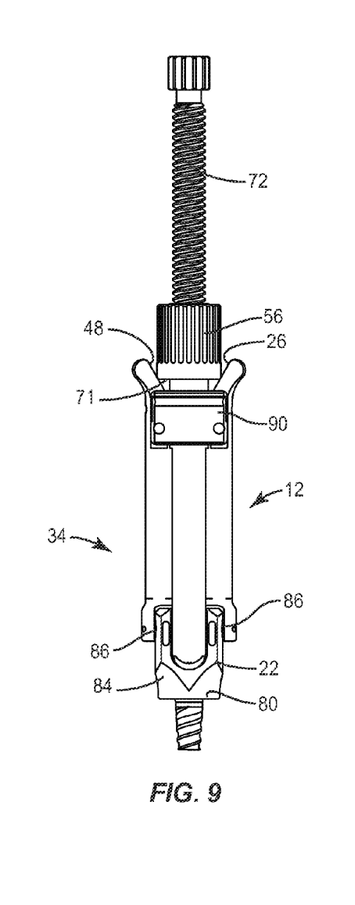
FIG. 9 is a plan view of components of one embodiment of a system in accordance with the principles of the present disclosure.
Figure 10:
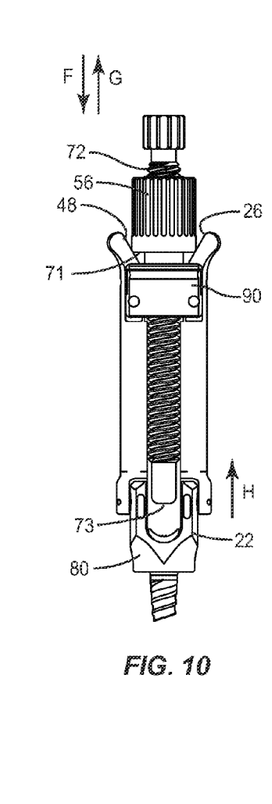
FIG. 10 is a plan view of the components shown in FIG. 9.

In one embodiment, as shown in FIGS. 8-10, spinal correction system 10, similar to that described above, includes a reducer 72 for employment with implant support 11. Reducer 72 includes an outer surface 74 defining a thread form 76 configured for engagement with threads 64 for axial translation of reducer 72 relative to part 54 for reducing an implant with bone fastener 22. In operation, reducer 72 is inserted through part 54 such that threads 76 engage threads 64. Reducer 72 includes a knurled handle that is rotated to translate reducer 72 axially in a proximal direction, as shown by arrow G in FIG. 10, and/or a distal direction, as shown by arrow F, relative to arms 12, 34 and body 52. Reducer 72 is translated such that an end surface 73 engages spinal rod 88 in a configuration to move spinal rod 88 relative to bone fastener 22 to drive spinal rod 88 into an implant cavity of receiver 80. As reducer 72 is manipulated, tabs 24, 44 engage cavities 86 of receiver 80 and receiver 80 is drawn, in the direction shown by arrow H in FIGS. 10 and 13, such that surface 73 is positioned to apply a force to spinal rod 88 so as to drive spinal rod 88 into receiver 80. In one embodiment, the knurled handle includes a tool socket for engagement with a surgical tool for rotating reducer 72.

In one embodiment, spinal correction system 10 includes spinal rod 88. Spinal rod 88 may have a semi-rigid, rigid or elastic configuration, and/or have elastic properties, such as the elastic properties corresponding to the material examples described above. In some embodiments, spinal rod 88 has a flexible configuration, which includes movement in a lateral or side to side direction and prevents expanding and/or extension in an axial direction upon fixation with vertebrae. In some embodiments, spinal rod 88 may be compressible in an axial direction. Spinal rod 88 can include a plurality of separately attachable or connectable portions or sections, or may be monolithically formed as a single continuous element. In some embodiments, spinal rod 88 is configured to extend over one or a plurality of vertebral levels.

Spinal rod 88 can have a uniform thickness/diameter. In some embodiments, spinal rod 88 may have various surface configurations, such as, for example, rough, threaded for connection with surgical instruments, arcuate, undulating, porous, semi-porous, dimpled, polished and/or textured according to the requirements of a particular application. In some embodiments, the thickness defined by spinal rod 88 may be uniformly increasing or decreasing, or have alternate diameter dimensions along its length. In some embodiments, spinal rod 88 may have various cross section configurations, such as, for example, oval, oblong, triangular, rectangular, square, polygonal, irregular, uniform, non-uniform, variable and/or tapered.

In some embodiments, spinal rod 88 can be secured at an appropriate angle to follow the curvature of a spine or to hold a desired position of a spine. Spinal rod 88 can be employed as provisional and/or working rod to temporarily support vertebrae V during a corrective procedure. In some embodiments, spinal correction system 10 may include one or a plurality of spinal rods 88. In some embodiments, the plurality of spinal rods 88 may be disposed in various alternate orientations, such as, for example, side by side, parallel, transverse and/or other angular orientations such as acute or obtuse, co-axial and/or may be offset or staggered.

Figure 11:
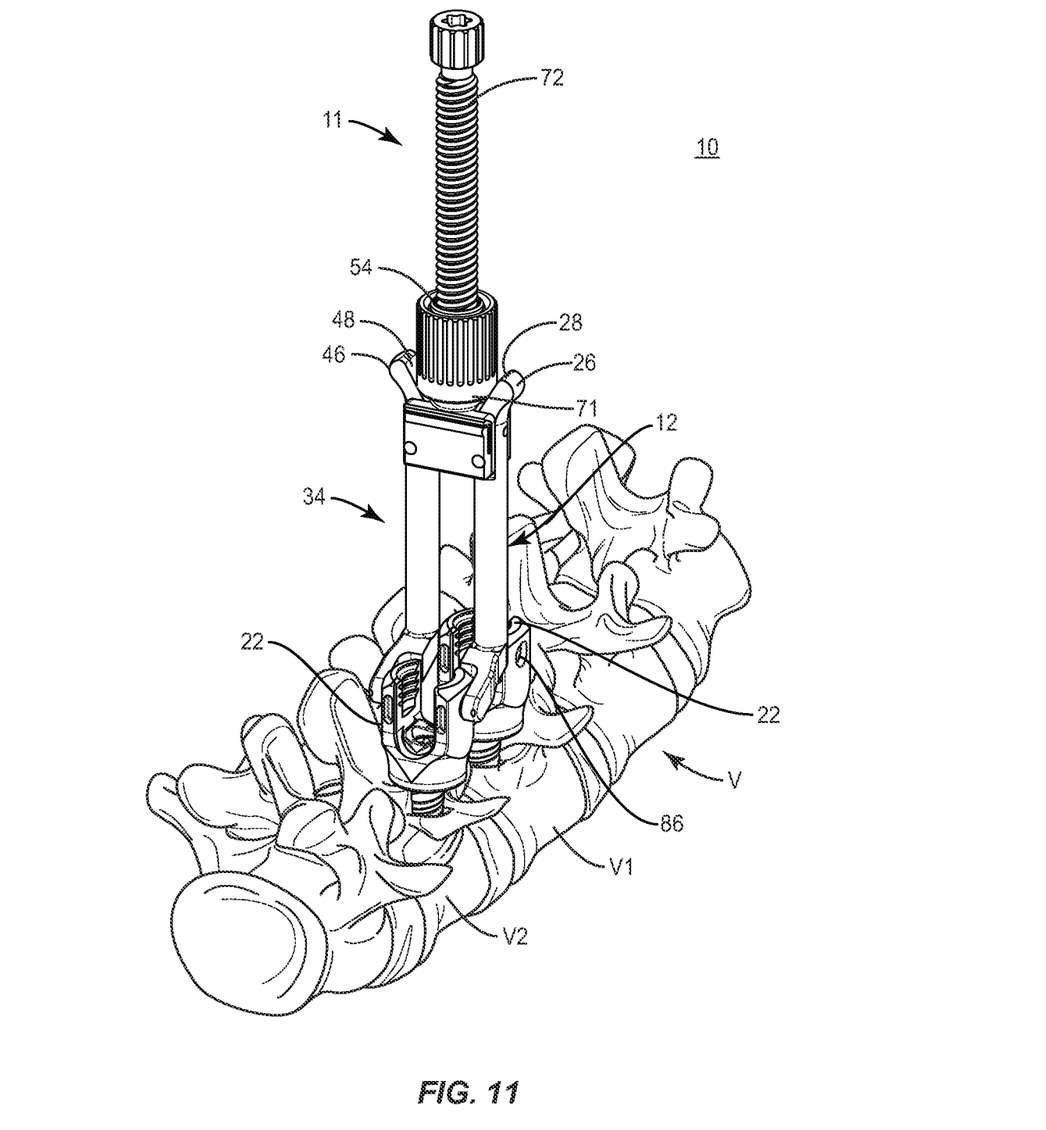
FIG. 11 is a perspective view of components of one embodiment of a system in accordance with the principles of the present disclosure disposed with vertebrae.
Figure 12:
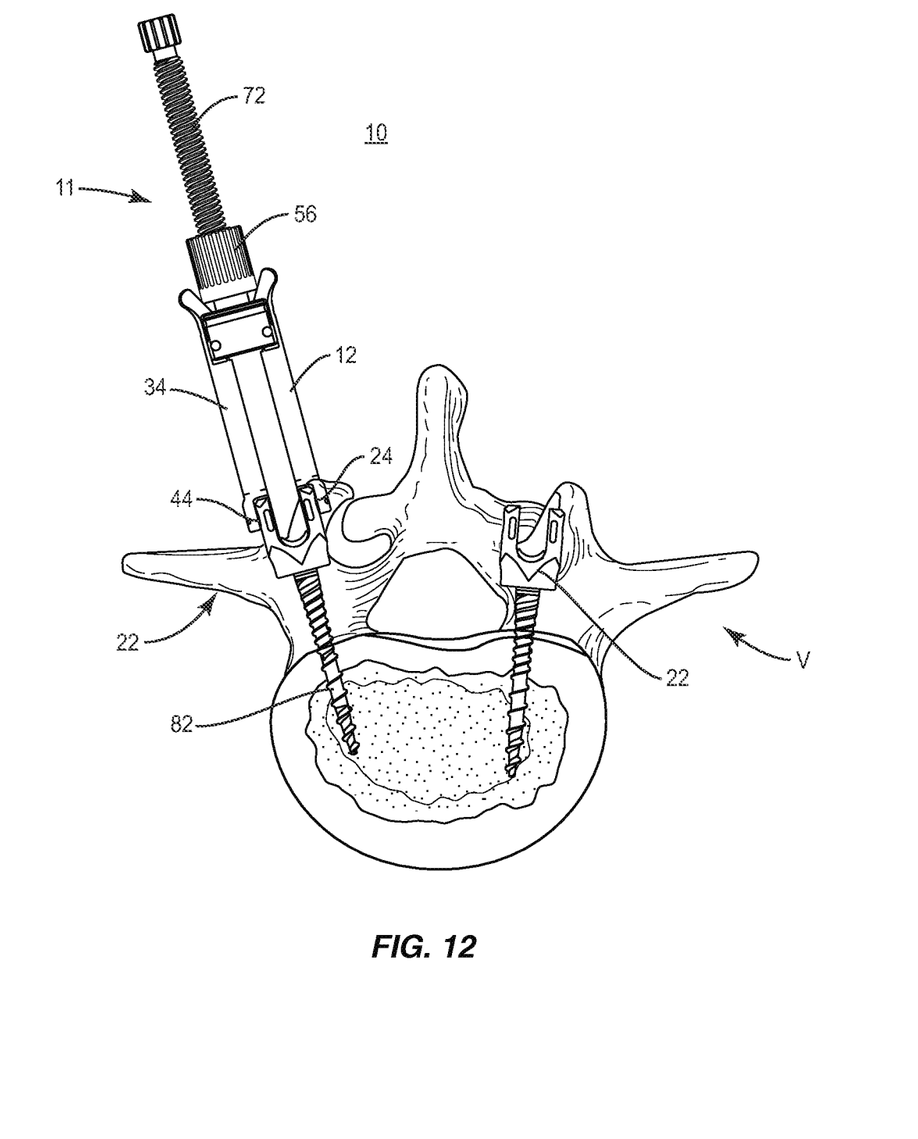
FIG. 12 is a plan view of the components and vertebrae shown in FIG. 11.

In assembly, operation and use, as shown in FIGS. 11-13, spinal correction system 10, similar to system 10 described herein, is employed with a surgical procedure, such as, for example, a correction treatment to treat AIS and/or Scheuermann's kyphosis of a spine. In some embodiments, one or all of the components of spinal correction system 10 can be delivered or utilized as a pre-assembled device or can be assembled in situ.

For example, spinal correction system 10 can be employed with a surgical correction treatment of an applicable condition or injury of an affected section of a spinal column and adjacent areas within a body, such as, for example, vertebral levels V1 and V2 of vertebrae V. In some embodiments, spinal correction system 10 may be employed with one or a plurality of vertebrae.

In use, a medical practitioner obtains access to a surgical site including vertebrae V in any appropriate manner, such as through incision and retraction of tissues. In some embodiments, spinal correction system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

One or a plurality of incisions are made in the body of a patient and a cutting instrument (not shown) creates one or a plurality of surgical pathways and/or openings for implantation of components of spinal correction system 10. A preparation instrument (not shown) can be employed to prepare tissue surfaces of vertebrae V, as well as for aspiration and irrigation of a surgical region.

Pilot holes (not shown) are made bilaterally in selected levels of vertebrae V, for example, vertebrae V1, V2 for receiving bone fasteners 22. Shafts 82 are inserted, drilled or otherwise fixed to vertebrae V1, V2 to attach bone fasteners 22 with vertebrae V. Implant supports 11 (only one implant support 11 is shown in FIGS. 11-13) are oriented for manipulation, alignment and capture of bone fasteners 22. In some embodiments, selected implant supports 11 are configured for disposal with bone fasteners 22 attached to a concave portion of selected vertebra of vertebrae V and selected implant supports 11 are configured for disposal with bone fasteners 22 attached to a convex portion of selected vertebra of vertebrae V, and/or may be connected to an apical portion of vertebrae V.

Implant support 11 is manipulable to the open configuration, as shown and described with regard to FIG. 3, from a closed configuration, as described herein. Arms 12, 34 rotate outwardly to the first configuration and the bias of springs 30, 35 is overcome such that arms 12, 34 are spaced apart to facilitate capture of receiver 80 of bone fastener 22. Ends 26, 46 are released and arms 12, 34 are biased to pivot to the second configuration, as shown and described with regard to FIG. 4. Tabs 24, 44 are removably fixed within cavities 86 and bone fastener 22 is releasably captured by arms 12, 34.

Part 56 is rotated clockwise, as shown and described with regard to FIG. 4, to translate part 56 axially into engagement with arms 12, 34. Surface 71 frictionally engages surfaces 28, 48 to fix the surfaces and lock arms 12, 34 in the second configuration, as shown in FIG. 11. Implant support 11 captures bone fastener 22 such that axis A1 is offset and disposed in a substantially parallel orientation relative to axis A2, as shown in FIG. 6 and described herein. Arms 12, 34 are rotatable about bone fastener 22 within a sagittal plane of vertebrae V between a first orientation such that axis A1 is substantially parallel with axis A2 of bone fastener 22 and a second orientation such that axis A1 is offset and disposed in a substantially transverse orientation relative to axis A2 of bone fastener 22. Rotation of arms 12, 34, in the sagittal plane of vertebrae V allows movement and/or pivoting of arms 12, 34 without interference, as discussed herein. In some embodiments, force is applied to implant supports 11, for example, via manipulation of a practitioner during a surgical treatment, to displace, pull, twist or align vertebrae V.

Reducer 72 is inserted through part 54 such that threads 76 engage threads 64, as shown in FIGS. 11-13. Reducer 72 is rotated to translate reducer 72 axially such that end surface 73 engages spinal rod 88 in a configuration to move spinal rod 88 relative to bone fastener 22 to drive spinal rod 88 into an implant cavity of receiver 80, as shown and described with regard to FIGS. 8-10. As reducer 72 is manipulated, tabs 24, 44 engage cavities 86 of receiver 80 and receiver 80 is drawn such that surface 73 is positioned to apply a force to spinal rod 88 so as to drive spinal rod 88 into receiver 80. In some embodiments, force is applied to implant supports 11, for example, via manipulation of a practitioner during a surgical treatment, to displace, pull, twist or align vertebrae V. Reducer 72 is rotated to translate reducer 72 axially such that end surface 73 disengages from spinal rod 88. In some embodiments, coupling members, such as, for example, set screws (not shown) secure spinal rod 88 with bone fasteners 22 to attach spinal rod 88 with vertebrae V without interference of implant support 11, as discussed herein.

To disengage implant support 11 from bone fastener 22, part 56 is rotated counter-clockwise, as shown and described with regard to FIG. 4, to translate part 56 axially out of engagement with arms 12, 34. From the closed configuration, a manipulative force or pressure is applied to ends 26, 46, such that arms 12, 34 rotate outwardly to the open configuration to facilitate release of bone fastener 22 from implant support 11.

In some embodiments, surgical correction system 10 includes an agent, which may be disposed, coated, packed or layered within, on or about the components and/or surfaces of surgical correction system 10. In some embodiments, the agent may include bone growth promoting material, such as, for example, bone graft to enhance fixation of the cage and/or fixation elements with vertebrae V. The components of surgical correction system 10 can be made of radiolucent materials such as polymers. Radiomarkers may be included for identification under x-ray, fluoroscopy, CT or other imaging techniques. In some embodiments, the agent may include one or a plurality of therapeutic agents and/or pharmacological agents for release, including sustained release, to treat, for example, pain, inflammation and degeneration. Upon completion of the procedure, the surgical instruments, assemblies and non-implant components of surgical correction system 10 are removed from the surgical site and the incision(s) is closed.

In some embodiments, the components of spinal correction system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal correction system 10 and methods of use may be used to prevent or minimize curve progression in individuals of various ages.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal correction system comprising:
a bone fastener comprising a receiver defining a longitudinal axis; and
an implant support comprising:
a body comprising a housing and a tubular part that defines a central longitudinal axis,
a first member including a first portion extending through the housing and a second portion configured to engage the receiver, the second portion extending in a transverse orientation from the first portion, and
a second member including a first portion extending through the housing and a second portion configured to engage the receiver, the second portion of the second member extending in a transverse orientation from the first portion of the second member,
wherein at least one of the members is movable relative to the central longitudinal axis between a first configuration and a second configuration such that the members are connected to the bone fastener and the central longitudinal axis is offset relative to the longitudinal axis.

2. A spinal correction system as recited in claim 1, wherein each of the members is rotatable relative to the central longitudinal axis between the first configuration and the second configuration.

3. A spinal correction system as recited in claim 1, wherein the second portion of the first member includes an inner surface that defines a support cavity configured for disposal of at least a portion of the bone fastener, the inner surface including a tab projecting into the support cavity for capture of the bone fastener.

4. A spinal correction system as recited in claim 3, wherein in the second configuration the support cavity includes a gap such that a portion of the inner surface is spaced from the bone fastener and the members are rotatable about the bone fastener within a plane of a body.

5. A spinal correction system as recited in claim 4, wherein the members are rotatable about the bone fastener within the plane between a first orientation such that the central longitudinal axis is substantially parallel with the longitudinal axis and a second orientation such that the central longitudinal axis is transverse to the longitudinal axis.

6. A spinal correction system as recited in claim 1, wherein the second portions each include an inner surface that defines a support cavity and includes a tab for capture of the bone fastener within the support cavity.

7. A spinal correction system as recited in claim 1, wherein the first portion includes a transverse end pivotable about the body.

8. A spinal correction system as recited in claim 1, wherein each of the first portions includes a transverse end pivotable about the body to facilitate rotation of the members relative to the central longitudinal axis between the first configuration and the second configuration.

9. A spinal correction system as recited in claim 1, wherein at least one of the members is resiliently biased to the second configuration.

10. A spinal correction system as recited in claim 1, wherein each of the members includes a spring to bias the members to the second configuration.

11. A spinal correction system as recited in claim 1, wherein the body includes a locking part translatable along the tubular part for engaging the members in the second configuration.

12. A spinal correction system as recited in claim 11, wherein the tubular part has an outer surface threaded with the locking part and an inner surface defining a thread form.

13. A spinal correction system as recited in claim 11, further comprising a reducer threaded with the inner surface of the tubular part for axial translation relative to the tubular part.

14. A spinal correction system as recited in claim 11, wherein the locking part has an outer gripping surface.

15. A spinal correction system as recited in claim 1, wherein the members are pivotable relative to the housing about pivot axes that extend parallel to the first portions.

16. A spinal correction system comprising:
a bone fastener comprising a receiver defining a longitudinal axis; and
an implant support comprising:
a body comprising a housing and a tubular part that defines a central longitudinal axis,
a first member including an extension extending through the housing and a leg extending transversely from the extension, the leg including an inner surface that defines a support cavity and a tab projecting therein, and a second member including an extension extending through the housing and a leg extending transversely from the extension of the second member, the leg of the second member including an inner surface that defines a support cavity and a tab projecting therein, wherein the extensions are pivotable about the tubular part between a first configuration and a second configuration such that the tabs capture a bone fastener within the support cavities and the axes are central longitudinal axis is offset relative to the longitudinal axis and the members are rotatable about the bone fastener within a sagittal plane of vertebrae.

17. A spinal correction system as recited in claim 16, wherein the members are rotatable about the bone fastener within the plane between a first orientation such that the central longitudinal axis is substantially parallel with the longitudinal axis and a second orientation such that the axes are central longitudinal axis is transverse to the longitudinal axis.

18. A spinal correction system as recited in claim 16, wherein the tubular part has an outer surface threaded with a locking part of the body and an inner surface defining a thread form.

19. A spinal correction system as recited in claim 18, further comprising a reducer threaded with the inner surface of the tubular part for axial translation relative to the tubular part.

20. A spinal correction system comprising:
   a bone fastener comprising a receiver defining a longitudinal axis and including an implant cavity;
   a spinal rod; and
   at least one implant support comprising;
      a body comprising a housing and a tubular part defining a central longitudinal axis,
      a first member including a first portion extending through the housing and a second portion extending in a transverse orientation from the first portion,
      a second member including a first portion extending through the housing and a second portion extending in a transverse orientation from the first portion of the second member, and
   a reducer disposable with the body,
   wherein the members are movable relative to the body between a first configuration and a second configuration such that the members are connected to the bone fastener and the central longitudinal axis is offset relative to the longitudinal axis and the members are rotatable about the bone fastener within a sagittal plane of vertebrae,
   in the second configuration, the reducer is axially translatable to engage the spinal rod for disposal within the implant cavity.

* * * * *